United States Patent
Triana et al.

(10) Patent No.: US 7,705,982 B2
(45) Date of Patent: Apr. 27, 2010

(54) METHODS AND APPARATUS FOR ANALYZING FLUID PROPERTIES OF EMULSIONS USING FLUORESCENCE SPECTROSCOPY

(75) Inventors: Jesus Alberto Canas Triana, Macae (BR); A. Ballard Andrews, Wilton, CT (US); Marc Schneider, Terre Haute, IN (US); Evie Freitas, Macae (BR); Oliver C. Mullins, Ridgefield, CT (US); ChenGang Xian, Abu Dhabi (AE); Andrew Carnegie, Beijing (CN); Jamil Al-Naser, Al-Ain (AE)

(73) Assignee: Schlumberger Technology Corporation, Ridgefield, CT (US)

( * ) Notice: Subject to any disclaimer, the term of this patent is extended or adjusted under 35 U.S.C. 154(b) by 465 days.

(21) Appl. No.: 11/563,293

(22) Filed: Jan. 26, 2007

(65) Prior Publication Data
US 2008/0037006 A1    Feb. 14, 2008

Related U.S. Application Data

(60) Provisional application No. 60/837,471, filed on Aug. 14, 2006.

(51) Int. Cl.
*G01J 3/30*    (2006.01)
(52) U.S. Cl. .................. 356/317; 356/436; 356/319; 356/326; 250/254; 250/256; 250/269.1
(58) Field of Classification Search ............ 250/269.1, 250/254, 255, 256, 302, 461.1; 356/326, 356/317, 319
See application file for complete search history.

(56) References Cited

U.S. PATENT DOCUMENTS

| | | | |
|---|---|---|---|
| 2,206,922 A | 7/1940 | Smith | |
| 2,334,475 A | 11/1943 | Claudet | |
| 2,346,481 A | 4/1944 | Garrison | |
| 4,609,821 A * | 9/1986 | Summers | 250/255 |
| 4,814,614 A * | 3/1989 | Tsui | 250/301 |
| 5,859,430 A | 1/1999 | Mullins et al. | |

(Continued)

FOREIGN PATENT DOCUMENTS

RU    2005107721 A    9/2005

(Continued)

OTHER PUBLICATIONS

Mullins et al ., "The Electronic Absorption Edge of Petroleum", Applied Spectroscopy, vol. 46, No. 9, 1992, pp. 1405-1411.

*Primary Examiner*—L. G Lauchman
(74) *Attorney, Agent, or Firm*—James M. McAleenan; Vincent P. Loccisano; Brigid M. Laffey

(57) ABSTRACT

This relates to methods and apparatus for analyzing samples by fluorescence spectroscopy. In one embodiment, the methods and apparatus use a fluorescence detection unit (FDU) of a composition fluid analyzer (CFA™) module to detect variations in fluid properties (gradients) within an oil bearing column. Some embodiments enable efficient downhole fluid analysis in heavy oils where water/oil emulsions are present (water in dispersed phase and oil in the continuous phase). The principles described herein may also be applied when there are fine particles in the oil such as from unconsolidated sands.

28 Claims, 10 Drawing Sheets

U.S. PATENT DOCUMENTS

| | | | |
|---|---|---|---|
| 5,912,459 A * | 6/1999 | Mullins et al. | 250/256 |
| 5,939,717 A | 8/1999 | Mullins | |
| 6,140,637 A | 10/2000 | Mullins et al. | |
| 6,268,603 B1 | 7/2001 | Mullins et al. | |
| 6,465,775 B2 | 10/2002 | Mullins et al. | |
| 6,678,050 B2 * | 1/2004 | Pope et al. | 356/435 |
| 6,704,109 B2 * | 3/2004 | Wu et al. | 356/417 |
| 7,084,392 B2 * | 8/2006 | DiFoggio et al. | 250/269.1 |
| 7,095,012 B2 | 8/2006 | Fujisawa et al. | |
| 7,173,239 B2 * | 2/2007 | DiFoggio | 250/269.1 |
| 7,214,933 B2 * | 5/2007 | DiFoggio et al. | 250/269.1 |

FOREIGN PATENT DOCUMENTS

| | | |
|---|---|---|
| RU | 2004139036 A | 1/2006 |

\* cited by examiner

METHODS AND APPARATUS FOR ANALYZING FLUID PROPERTIES OF EMULSIONS USING FLUORESCENCE SPECTROSCOPY

RELATED APPLICATIONS

This claims priority of U.S. provisional patent application No. 60/837,471 filed Aug. 14, 2006 and entitled "Methods and Apparatus for Analyzing Fluid Properties of Emulsions Using Fluorescence Spectroscopy."

FIELD

This invention relates to sample analysis by fluorescence spectroscopy.

BACKGROUND

The study of hydrocarbon fluorescence for the purpose of downhole formation fluid evaluation using a wireline logging tool has been proposed in numerous patents (e.g. U.S. Pat. Nos. 2,206,922; 2,346,481; 2,334,475; 6,140,637; and 6,268,603, each of which is incorporated by this reference). As described in one or more of the patents identified above, the proposed methods are generally directed to moving a wireline logging tool through a borehole while irradiating the formation. The methods teach detecting fluorescence through an optically transparent material, which is pressed against the borehole wall. However, in order to be useful to any degree, the transparent material must be pressed against the borehole wall with sufficient force to displace the mud cake. Unfortunately, the natural fluorescence of certain shale and hydrocarbon bearing rocks complicates the interpretation of the logs and the methods taught by the prior art have not been widely adopted.

Schlumberger's Modular Formation Dynamics Tester (MDT™) collects multiple samples at any number of stations in a well. Formation fluids are hydraulically isolated from the drilling fluids (and the mud cake) in the well. The formation fluid is drawn into a flow line inside the MDT tool body and analyzed using absorption spectroscopy through a sapphire optical cell. Contamination monitoring tells the operator when to capture a sample. GOR (Gas/Oil Ratio—the ratio of produced gas to produced oil) and compositional information can be determined by the LFA™ tool and CFA™ tool respectively. However, because the number of available sample bottles contained by the MDT is limited, some have proposed a quasi-continuous log of the formation fluids that could be generated without sample collection. Taking a quasi-continuous log without sample collection is generally referred to as "gargling". Gargling methods are discussed in U.S. Pat. Nos. 6,476,384; 6,465,775; 5,859,430; and 5,939,717, each of which is incorporated by this reference.

SUMMARY

The present disclosure addresses weaknesses of the prior art described above. Specifically, one embodiment provides a method of analyzing fluid properties. The method comprises providing a downhole fluid analysis tool, extracting a fluid from a downhole formation with the downhole fluid analysis tool, flowing the fluid into the downhole fluid analysis tool, and acquiring a fluorescence signal (i.e. any fluorescence data) from the fluid while downhole. In one embodiment, acquiring a fluorescence signal comprises irradiating the fluid through an optical cell and detecting fluorescence. One embodiment of the method further includes moving the downhole fluid analysis tool through a borehole, and performing the extracting, flowing, and acquiring at multiple locations along the borehole.

In one embodiment, the method further comprises identifying fluid compositional gradients in a fluid column by comparing the fluorescence signals at two or more of the multiple locations along the borehole. One method further comprises flowing the fluid back out of the downhole fluid analysis tool and generating a quasi-continuous log of the fluid without collecting samples. In one embodiment, the method further comprises comparing the fluorescence signal to known fluorescence spectra and identifying the fluid based on the comparison of the fluorescence signal of the fluid to the known fluorescence spectra. In one embodiment, the method further comprises comparing the fluorescence signal to known fluorescence spectra while downhole, and identifying the fluid based on the comparison of the fluorescence signal of the fluid to the known fluorescence spectra while downhole. One embodiment further comprises correlating the fluorescence signal and other physical characteristics of the fluid to generate a database. The other physical characteristics may comprise one or more of asphaltene weight fraction, density, viscosity, and C36+.

One embodiment of the method of analyzing fluid properties further comprises correlating the fluorescence signal with other well-logging or logging-while-drilling data. One embodiment further includes identifying relationships between the fluorescence signal and the well-logging or logging-while-drilling data. Another embodiment further comprises correlating the fluorescence signal with other well-logging or logging-while-drilling data and creating models or tables to assist in interpreting the fluorescence signal.

One aspect provides a method of identifying fluid compositional gradients in an oil column. The method comprises moving a fluid analysis tool through a borehole, setting the fluid analysis tool at a desired sampling interval, extracting a fluid from a formation adjacent to the borehole into a flowline in a body of the tool, irradiating the fluid in the flowline through an optical cell inserted in the flowline, and detecting fluorescence. In one embodiment, the method comprises identifying fluid compositional gradients in a fluid column by comparing the fluorescence signals along the sampling interval. Some embodiments further comprise comparing the detected fluorescence to known fluorescence spectra and identifying the fluid based on the comparison of the detected fluorescence to the known fluorescence spectra. According to one embodiment, a distance between the settings on the sampling interval is regular or irregular. In one embodiment, the irradiation is accomplished with UV wavelength light.

One aspect provides a method of analyzing a sample, comprising acquiring fluorescence data from a formation sample while downhole at multiple stations, and analyzing changes in fluorescence at two or more of the multiple stations to determine whether the sample is the same or different at two or more of the multiple locations. One embodiment further comprises measuring color of the formation sample at the multiple stations and relating changes in the fluorescence data to changes in fluid color. One embodiment further comprises using changes in the fluorescence data to determine if there are fluid compartments within a formation. In one embodiment the method further comprises analyzing a structure of the fluorescence data over an extended depth interval and producing an indication of a physical property correlated with fluorescence. In one embodiment the method further comprises correlating the fluorescence data with other well-logging data, identifying relationships between the fluorescence data and other well-logging data, and creating models or rules to assist in interpretation of other downhole logs. In some embodiments, fluorescence data may form a quasi-continuous log. Moreover, the formation sample may contain a water/oil emulsion.

One embodiment provides an apparatus comprising a downhole fluid analysis tool. The downhole fluid analysis tool comprises a fluid extraction module comprising a flowline, an optical cell disposed in the flowline, an irradiation source at the optical cell, and a fluorescence detection unit at the optical cell. One embodiment also includes a fluid color measurement module. In one embodiment, the irradiation source comprises an LED or laser diode capable of producing visible, ultraviolet, and/or infrared light.

One aspect provides a method comprising retrofitting an existing downhole fluid analysis tool with a fluorescence detection unit. The method may include retrofitting the downhole fluid analysis tool with a UV light source.

Some aspects provide method and apparatus for identifying fluid compositional gradients in an oil column using fluorescence spectroscopy, which may or may not contain an emulsion. One method comprises moving a tool through the borehole, setting the tool at the desired sampling interval, extracting a fluid from the formation into the body of the tool, irradiating the fluid in the flowline through an optical cell inserted in the flowline, and detecting the fluorescence. The light source can be visible, ultraviolet or infrared or any combinations of these. These light source(s) can be an LED(s) or laser diode(s). The fluorescence signal is detected at the front surface of the optical cell.

The description below establishes a relationship between a metric extracted from a fluorescence signal or spectrum, such as a band area or a peak height, and a desired property of the oil. Within an oil column, the correlation between the fluorescence and the color of the oil is such that the metric can be used to detect changes in the fluid composition and/or concentration changes within the oil column. Thus, from the variation in the fluorescence signal, one may ascertain whether compositional gradients exist within a sand body, and furthermore identify fluid compartments (in particular, heavy oil columns are often graded due to biodegradation).

Some aspects apply to heavy oils in which a water/oil emulsion has been created due to the water based muds used for drilling. Emulsions effect absorption measurements because water droplets scatter the light, preventing it from reaching the detector. However, one skilled in the art will recognize that fluorescence can be used instead to map compositional and other property changes (for example, fluorescence can be correlated with oil color or other properties or data).

One aspect utilizes this technique to perform quasi-continuous well logging without collecting samples, in order to rapidly detect compositional variations within an oil column. One aspect improves GOR and composition analysis.

BRIEF DESCRIPTION OF THE DRAWINGS

The accompanying drawings illustrate certain embodiments and are a part of the specification.

Figure 1:
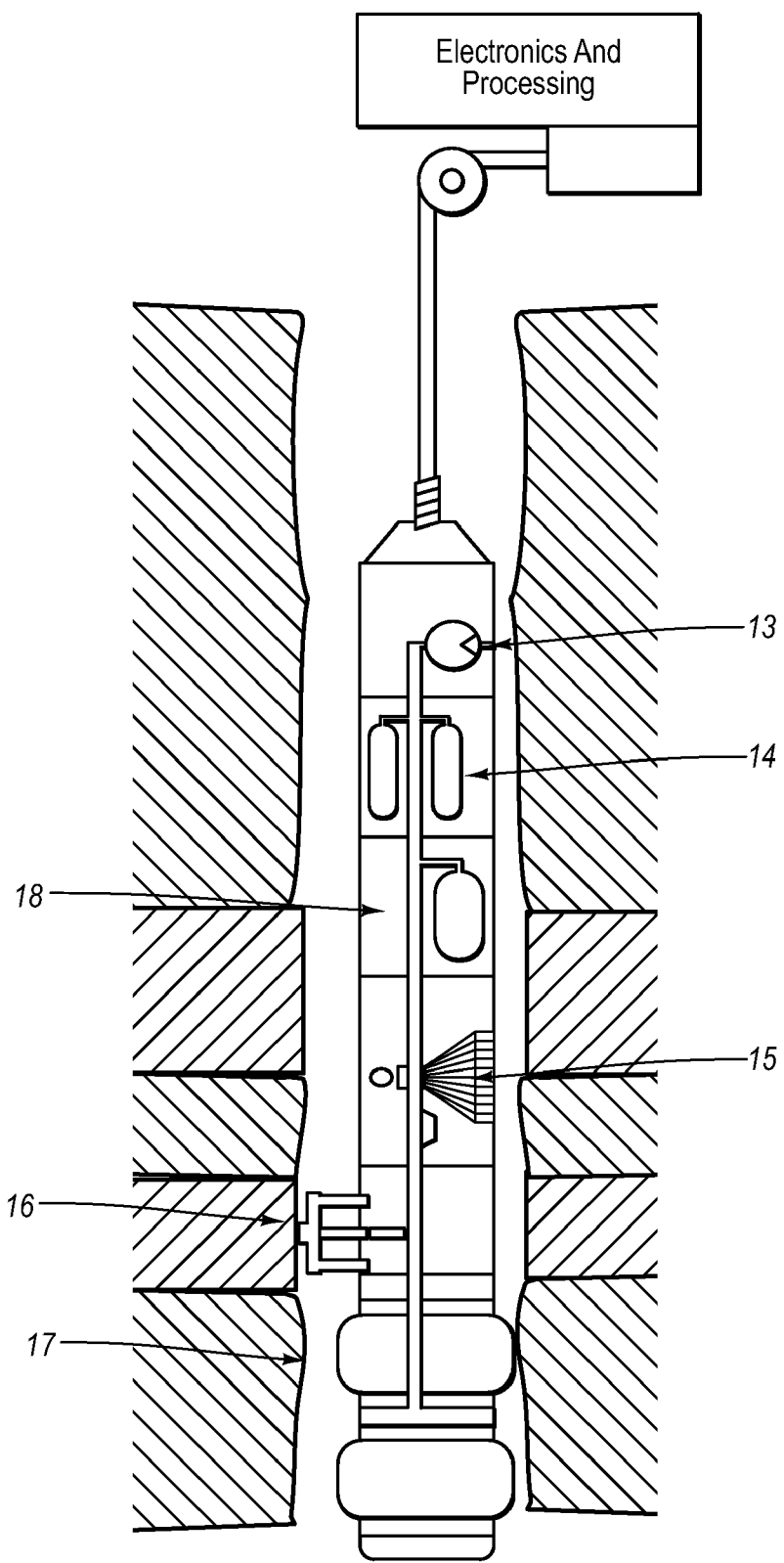
FIG. 1 shows an MDT instrument in a borehole that may be retrofitted or provided with a fluorescence detector unit (FDU), such as the FDU shown in FIG. 2.

Throughout the drawings, identical reference numbers indicate similar, but not necessarily identical elements. While the principles described herein are susceptible to various modifications and alternative forms, specific embodiments have been shown by way of example in the drawings and will be described in detail herein. However, it should be understood that the invention is not intended to be limited to the particular forms disclosed. Rather, the invention includes all modifications, equivalents and alternatives falling within the scope of the appended claims.

DETAILED DESCRIPTION

Illustrative embodiments and aspects of the invention are described below. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such a development effort might be complex and time-consuming, but would nevertheless be a routine undertaking for those of ordinary skill in the art having the benefit of this disclosure.

Reference throughout the specification to "one embodiment," "an embodiment," "some embodiments," "one aspect," "an aspect," or "some aspects" means that a particular feature, structure, method, or characteristic described in connection with the embodiment or aspect is included in at least one embodiment of the present invention. Thus, the appearance of the phrases "in one embodiment" or "in an embodiment" or "in some embodiments" in various places throughout the specification are not necessarily all referring to the same embodiment. Furthermore, the particular features, structures, methods, or characteristics may be combined in any suitable manner in one or more embodiments. The words "including" and "having" shall have the same meaning as the word "comprising."

Moreover, inventive aspects lie in less than all features of a single disclosed embodiment. Thus, the claims following the Detailed Description are hereby expressly incorporated into this Detailed Description, with each claim standing on its own as a separate embodiment of this invention.

One advantage of Schlumberger's composition fluid analyzer (CFA™) lies in its ability to detect compositional fluid gradients within an oil column. Compositional gradients can occur due to a variety of sources: biodegradation, gravity, thermal and/or diffusion gradients can all contribute. Fluid gradients may also exhibit discontinuities, signaling the presence of compartments in reservoirs that were previously assumed to be homogeneous—a leading cause of production shortfall in the petroleum industry today.

In light oils, compositional gradients are detected primarily by variations in the GOR ratio. In heavy oils, GOR variation is less significant and compositional gradients are detected by differences in the location of the absorption edge (i.e. color). Heavy oil columns are known to be biodegraded due to the fact that heavy oils result from low temperature catagenesis, and the biodegrading bacteria survive well at low temperature. In spite of this known compositional variation, operational difficulties with heavy oil sampling in water based muds precludes proper analysis of the heavy oils in the column.

Problems arise because heavy oils are commonly drilled with water based muds, which form stable water/oil emulsions due to the interfacial activity of resins and asphaltenes. The emulsions have even higher viscosity than the naturally high viscosity of the original heavy oil. To make matters worse, the flow of a heavy oil emulsion through porous media exacerbates the problem due to effective throat plugging by interfacial tension. Consequently, invaded water flows preferentially, and oil entry into fluid analysis or sampling tool is retarded, resulting in longer cleanup times.

Emulsions affect the optical measurements because absorption spectroscopy (Beer-Lambert law) is highly sensitive to the presence of water droplets and particulates in the flow line. The intensity of the scattering scales rapidly with increasing water fraction and is generally wavelength dependent. The negative effect is enhanced in the forward direction, toward the detector. Because color subtraction is important for GOR and composition analysis, emulsions compromise the accuracy of both Schlumberger's LFA™ (Live Fluid Analyzer) and CFA™ measurements. Even for relatively small water fractions, it is difficult to correct for the noise created by the scattering in the absorption spectra.

One aspect described herein uses a correlation between the color of the formations sample or fluids such as crude oil (absorption) and the sample fluid fluorescence. Some aspects, however, may utilize fluorescence data by itself or in combination with other data. Color characteristics of samples such as crude oils are known to those of ordinary skill in the art having the benefit of this disclosure. However, in emulsified heavy oils, light scattering causes deterioration in the S/N (signal-to-noise) so that crude oil color cannot be accurately determined from the absorption spectra. Thus, there is a need for a more reliable technique to characterize fluids and/or detect compositional gradients in emulsified heavy oil columns. Accordingly, one aspect describes a method of using an FDU (for example an FDU of a CFA™ or any comparable optical fluorescence device) to collect a fluorescence signal or fluorescence data downhole. The fluorescence measurements may be made inside the tool on formations fluids, rather than irradiating borehole walls. For example, Schlumberger's MDT tool may be used and/or modified to collect or extract formation sample fluids for fluorescence analysis (and possibly other analysis—such as color analysis).

Crude oil color is due to photon absorption by polycyclic aromatic hydrocarbons (PAHs). An excited PAH may decay back to the ground state either by re-emitting a photon at a longer wavelength (fluorescence) through non-radiative relaxation (thermal vibrations) or by collisional energy transfer (kinetics). Thus, fluorescence is intimately related to absorption, and the fluorescence intensity is found to be correlated with crude oil color. Since the oil color can be used to detect fluid gradients and fluid compartments in heavy oils, fluorescence may alternatively be used to reveal compositional variations or identify or otherwise characterize formation fluids downhole. However, the correlation between fluorescence and oil color is not trivial. For example, an increase in chromophore concentration in oil results in an increase in color but a decrease in fluorescence. That is, increasing the fluorophore concentration of a crude oil decreases fluorescence. This counterintuitive effect is largely due to intermolecular fluorescence quenching interactions mediated by diffusion and aggregation formation.

Generally speaking, detailed composition and/or concentration information cannot be determined from oil color alone, but relative variations in the concentrations of heavy ends (e.g. asphaltenes) produce large changes in the coloration and associated fluorescence. Hence, it is possible in some circumstances to correlate changes in crude oil color (or fluorescence) with changes in composition and/or concentration. It is also possible to compare fluorescence data downhole with fluorescence data of a known sample from laboratory analysis, provided a careful calibration of the instrument is done in the laboratory beforehand.

Even after a downhole fluid analysis or sampling tool is properly positioned in a borehole, it can take up to fifteen hours of pumping to clean a tool sample flowline, perform accurate optical transmission measurements, and acquire a sample. The long time duration precludes all but the most rudimentary evaluation of compositional variation in heavy oil columns drilled with water based muds. However, for DFA (downhole fluid analysis) purposes, often one does not need a sample, just the analysis. Fluorescence requires only an oil film on an analysis optical cell or window. Oil films find their way onto optical cells or windows early in the flowline cleanup stage, making downhole fluorescence measurement and analysis an attractive data measurement.

It is advantageous to collect the fluorescence signal using a front surface geometry for several reasons. Heavy oils are opaque at visible wavelengths and in a front surface geometry and self absorption affects are minimized. Also the comparatively short escape depth of the fluorescent photons in heavy oils ensures that the fluorescence measurement will be less affected by light scattering than the corresponding absorption measurement.

A long wavelength absorption edge for most crude oils results from polycyclic aromatic hydrocarbons (PAH). The coloration is linearly dependent on the concentration of these chromophores in accord with Beers law $$A \propto \log \frac{I}{I_o} \propto \sum_i \epsilon_i c_i l \quad (1)$$

where: A is absorption, $I_o$ the incident light intensity,

I the transmitted light intensity, $\epsilon_i$ is the molar extinction coefficient for component i, and $c_i$ is the concentration of component i and l is the pathlength.

In crude oils, quenching rate constants are diffusion limited. The Stern-Volmer equation is obtained from analysis of the excited state decay rate:

$$\frac{I_{Fo}}{I_F} - 1 = \frac{k_Q}{k_{Fo}}[Q] \qquad (2)$$

where: $k_F$ is the excited state decay rate and the measured fluorescence decay rate, $k_{Fo}$ is the intrinsic fluorescence decay rate in the absence of quenchers,

[Q] is the quencher concentration, and $k_Q$ is the diffusional quenching rate constant.

Equation 2 shows that, for IFo>>IF (which applies for crude oils), the fluorescence intensity for a concentrated sample is proportional to the quencher concentration. The quenchers are the large PAHs that have red shifted electronic transitions, i.e., the same molecular fractions that give rise to crude oil coloration.

It can be shown that to the zeroth order, both crude oil coloration (Eq. 1) and crude oil fluorescence intensity (Eq. 2) are linearly dependent on large PAH chromophore population. Thus, for solutions of a given crude oil, one can quantitatively relate coloration and fluorescence intensity.

Crude oil quantum yields are higher at UV excitation wavelengths (e.g. 350 nm) than visible wavelengths (e.g. 450 nm). Also, greater differences in the fluorescence spectra of crude oils are observed at shorter excitation wavelengths. In addition, UV photons have a shorter escape depth than visible photons, so fluorescence spectra are less affected by the emulsions. Therefore, one embodiment of the present invention employs one or more UV LED or laser diode sources downhole on a fluid analysis tool (rather than, for example, blue). A UV light source may be retrofitted on a fluid analysis tool or originally presented. Nevertheless, one skilled in the art will readily recognize that any excitation wavelength may be used according to the principles described herein. In view of this, the present invention is not intended to be limited to those embodiments recited herein.

FIG. 1 diagrammatically illustrates one embodiment of a downhole fluid analysis, sampling, and testing tool in a borehole. In the embodiment of FIG. 1, the tool comprises a packer module 17 and a flowline 18. The flowline 18 extends through the tool substantially longitudinally to a pumpout module 13 at a first or upper end. A probe module 16 facilitates fluid communication between the adjacent formation and the flowline 18. A spectroscopy module 15 (and/or an FDU) may be connected in series to the flowline 18 (see FIG. 2). Sample chambers 14 may be connected to the flowline 18 and (if included) may receive and store fluid samples from the formation.

Figure 2:
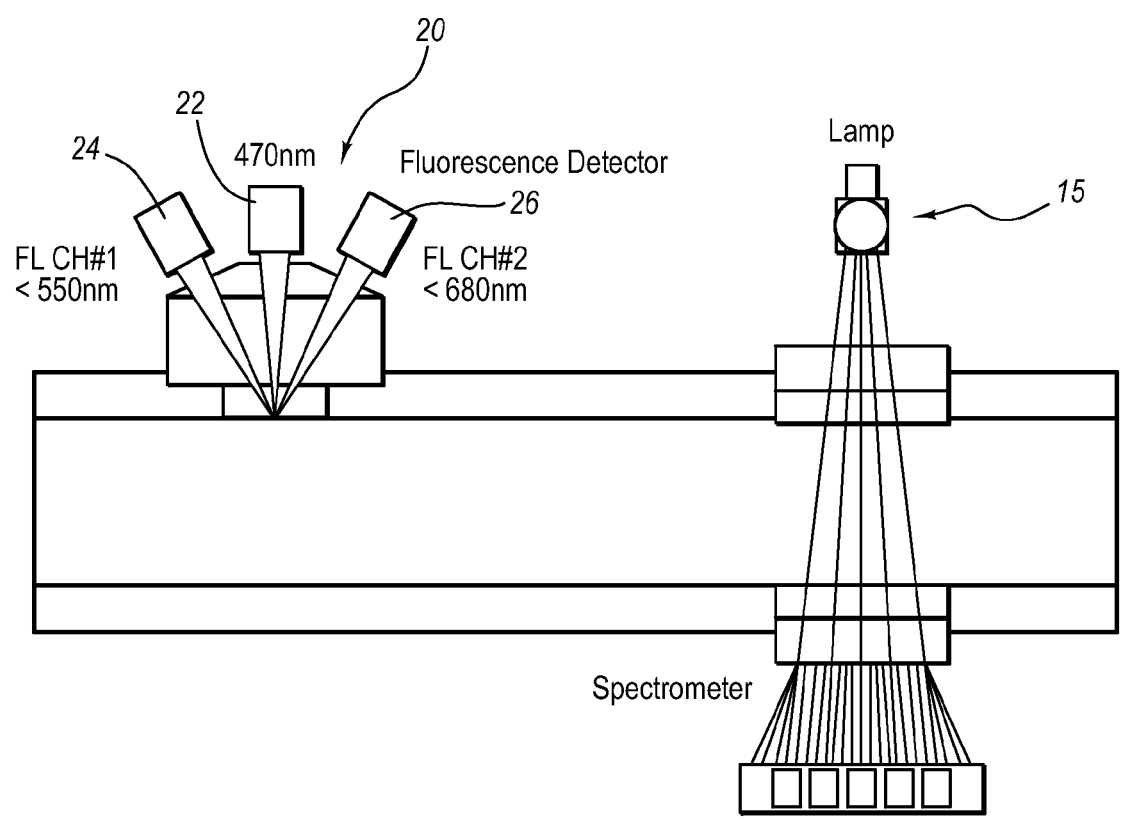
FIG. 2 shows a schematic of a CFA™ absorption spectrometer and an FDU.

FIG. 2 is a schematic diagram of the CFA™ absorption spectrometer 15 and the FDU 20. The FDU 20 may comprise a light source 22, and the light source 22 may comprise an LED or laser producing light at, for example a wavelength of approximately 470 nm. The FDU 20 includes one or more fluorescence detectors, such as first and second detectors 24, 26. The first and second detectors 24, 26 may comprise Si photodiodes and may include two long pass optical filters which transmit light above, for example, about 550 nm and 650 nm, respectively. However, it will be understood by those of ordinary skill in the art having the benefit of this disclosure that the principles described herein are not limited to this particular apparatus or the particular wavelengths discussed. There may be any number of different embodiments of the FDU 20. For example, in another embodiment, multiple light sources with different wavelengths and multiple detectors are possible. The apparatus of FIG. 2 may be implemented with any fluid analysis tool, such as the tool shown in FIG. 1

Figure 3:
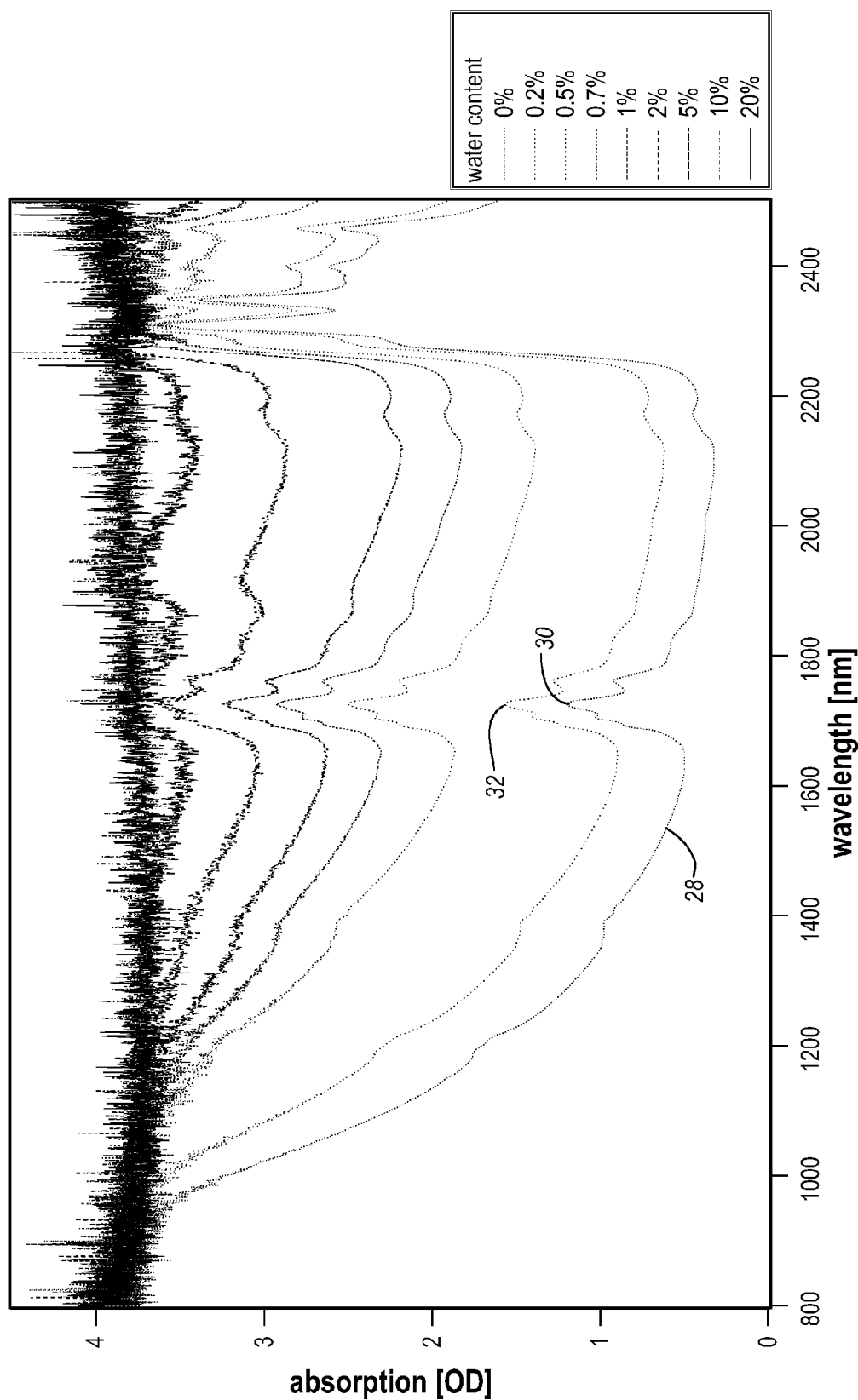
FIG. 3 shows the effect of a water/oil emulsion on the absorption spectra of a heavy oil from a geographic region in the Middle East.

FIG. 3 shows the effect of a water/oil emulsion on the absorption spectra of a heavy oil from a geographic region in the Middle East. A first line 28 shows clean absorption spectra of heavy oil from a geographic region in the Middle East. Additional lines illustrate absorption spectra with increasing water fractions. The light scattering from water droplets (several microns in diameter) scales with the increasing water fraction. The peaks 30, 32 etc. at 1725 and 1760 nm are vibrational hydrocarbon molecules. Water has vibrational bands at 1445 and 2000 nm.

Figure 4:
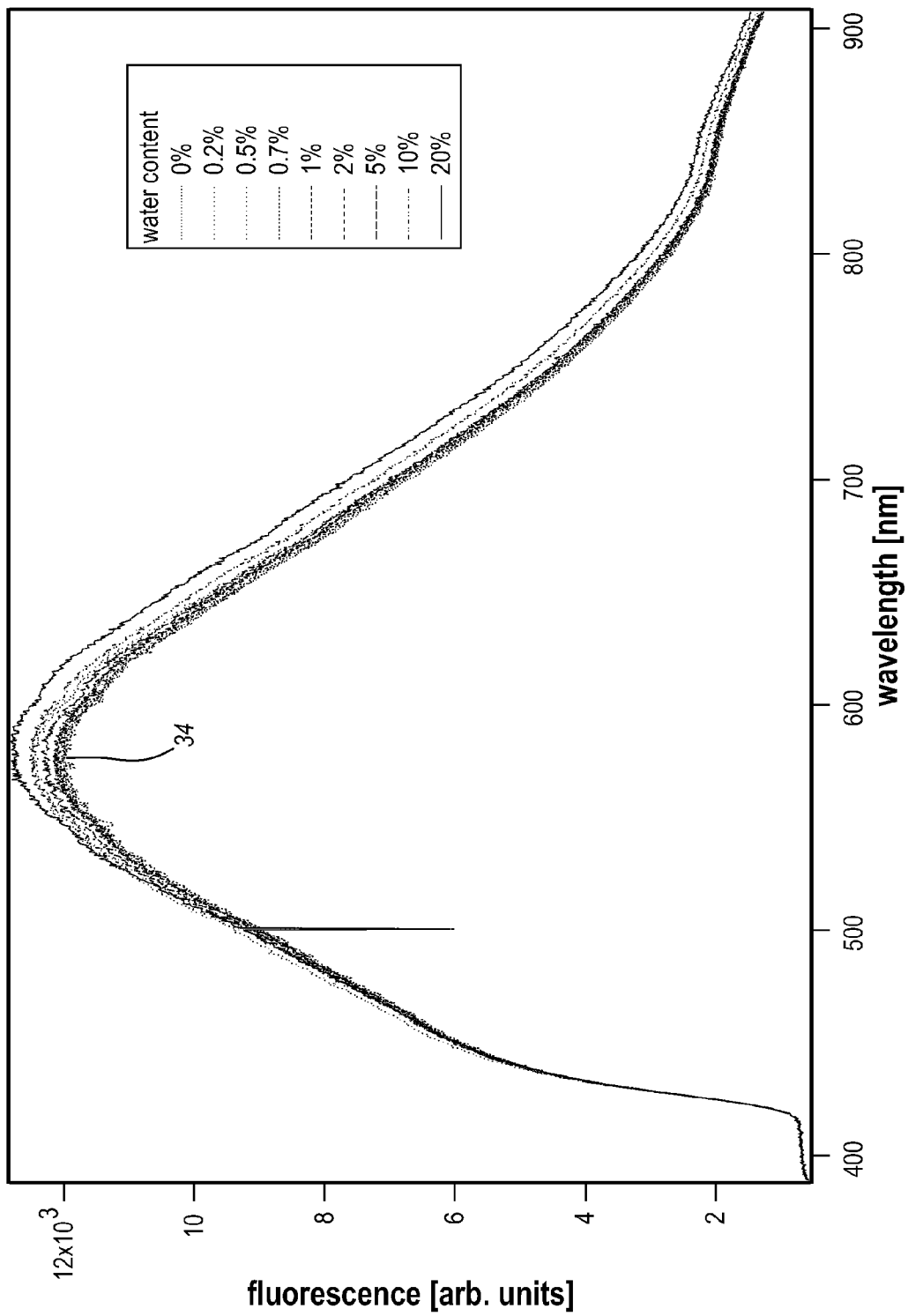
FIG. 4 shows fluorescence spectra for the same heavy oil associated with FIG. 3 with the same water fractions.

FIG. 4 shows fluorescence spectra of the same heavy oil of FIG. 3 with the same water fractions. The first line 34 shows clean fluorescence spectra of heavy oil from a geographic region in the Middle East. Remaining lines show spectra with increasing water fractions. Compared with the absorption spectra shown in FIG. 3, the fluorescence spectra of FIG. 4 is much less sensitive to the emulsion or water content of a sample.

Fluorescence signals, as illustrated in the present invention, are less sensitive to an emulsion. In one aspect, this insensitivity of fluorescence to emulsions is exploited (in lieu of absorbance) and used to map color gradients in an oil column which reflect compositional changes. These color gradients (i.e., the ones that exist because of composition changes) can in turn be correlated with other physical properties of the oil such as asphaltene content.

Figure 5:
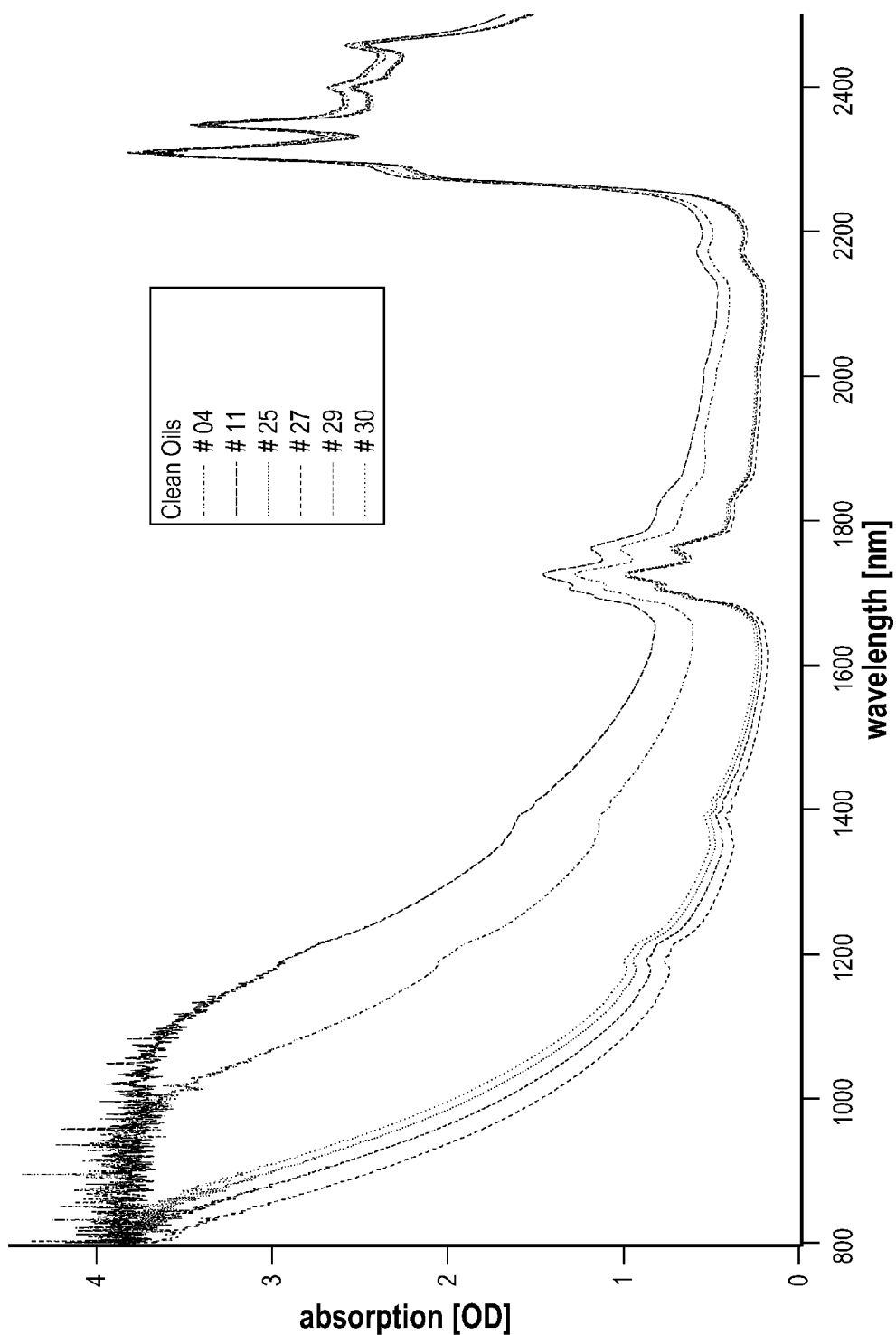
FIG. 5 shows the absorption spectra of six Middle Eastern dead oils with different amounts of asphaltene content.
Figure 6:
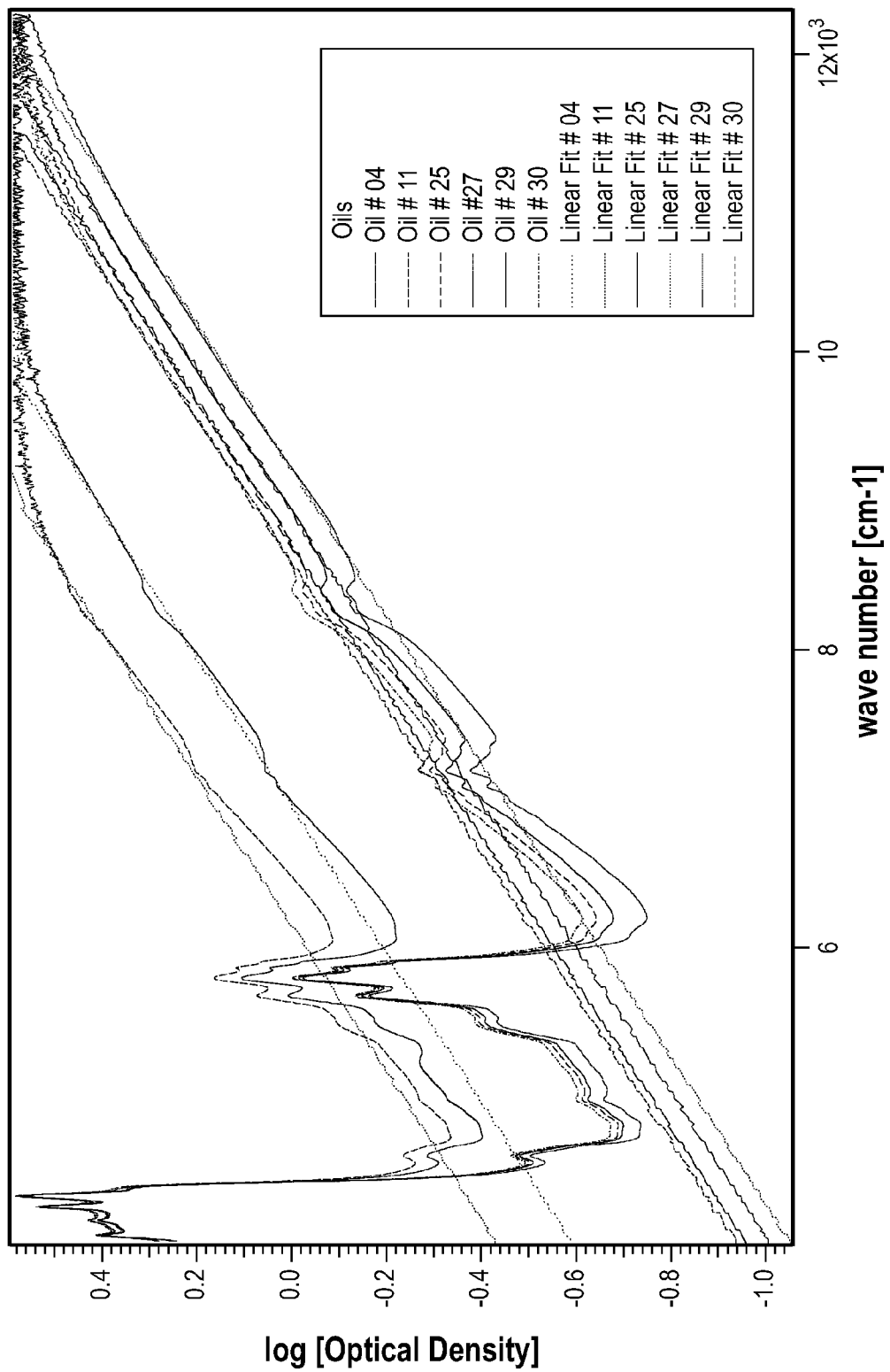
FIG. 6 is a plot of the log of the OD vs. wave number, for the same six oils in FIG. 5.

FIG. 5 shows the absorption spectra of six Middle Eastern dead oils with different amounts of asphaltene content. From left to right, the asphaltene fraction increases from 3-13%. The vibrational overtone bands are centered at 1725 nm. The location of the electronic absorption edge reflects the population distribution of the aromatic components in the crude oil. Plotting the log of the OD (optical density) vs. wavelength (FIG. 6) shows that the slope of the absorption edge is the same for all six crude oil samples. By fitting the electronic absorption edge with a linear equation of the form:

$$\log OD = \log \alpha + \beta/\lambda$$

One can obtain a single number which characterizes the relative color variation across the entire data set. This is referred to as the absorption intercept parameter (AIP).

Figure 7:
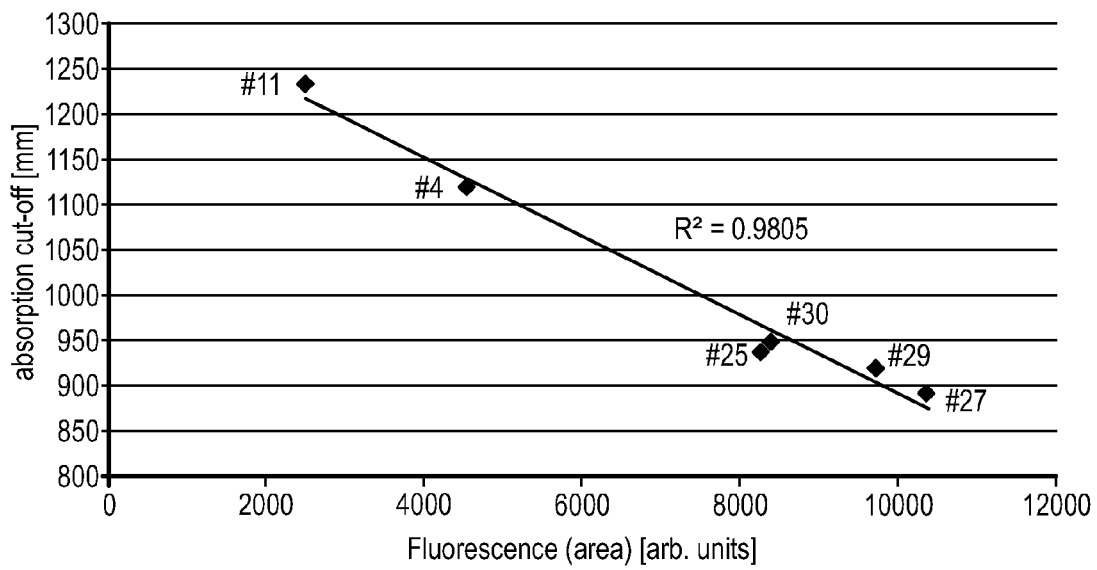
FIG. 7 is a plot of the correlation between the AIP (absorption intercept parameter) and the total fluorescence intensity (TFI) for the six oils identified in FIG. 5.

FIG. 7 is a plot of the correlation between the AIP (absorption) and the total fluorescence intensity (TFI) for the six oils mentioned above. The correlation is:

$$AIP = -1.0905 * TFI - 1.0557$$

$$R^2 = 0.99$$

Thus, a single parameter (AIP) characterizing the color of the oil correlates strongly with a single parameter characterizing the fluorescence response (TFI). Accordingly, in some embodiments absorption and fluorescence can be used interchangeably as an indicator of relative fluid coloration.

Figure 8:
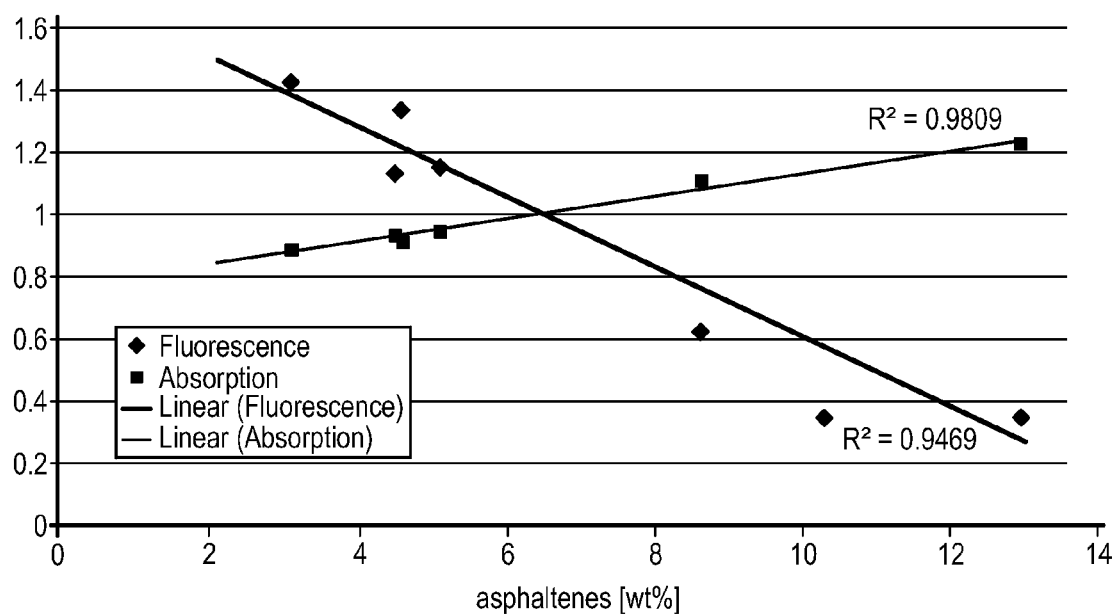
FIG. 8 plots the correlation between the AIP and the total TFI and the asphaltene wt % for the six different oils identified in FIG. 5.

FIG. 8 plots the correlation between the AIP and the total fluorescence intensity (TFI) and the asphaltene wt % for these six different oils. For the AIP the correlation is:

$$AIP = 0.0682 * \text{Asphaltene wt\%} - 2.0957$$

$$R^2 = 0.97$$

For the fluorescence the correlation is:

$$TFI = -0.0616 * \text{Asphaltene wt\%} + 0.9476$$

$$R^2 = 0.952$$

Thus both the AIP and FTI are sensitive to compositional variations. It is expected that these correlations will strengthen when the data are restricted to a single basin. It is also expected that these correlations will further improve when the data are restricted to an individual well. Other correlations may be discovered by those of ordinary skill in the art having the benefit of this disclosure with routine experimentation following the principles described herein, such as between the TFI and C36+ weight fraction, the TFI and density, TFI and composition, and the TFI and viscosity.

Fluorescence logs may be acquired either by logging the entire well in a quasi-continuous mode, without collecting samples, or samples could be captured when the operator decides that the fluid has changed composition. For example, an operator may compare the fluorescence logs at stations A and B. If the fluorescence logs are identical, then the tool is moved to a new location C and the test is repeated. On the other hand, if the fluorescence signal has increased or decreased, then the operator may decide whether to capture a sample based on his knowledge of the formation. The operator may cross-correlate the variation in the fluorescence response with other logs to improve the interpretation. Using a calibrated database for a specific basin, the operator may further relate the fluorescence logs to changes in the composition, density, viscosity and other physical properties.

Figure 9:
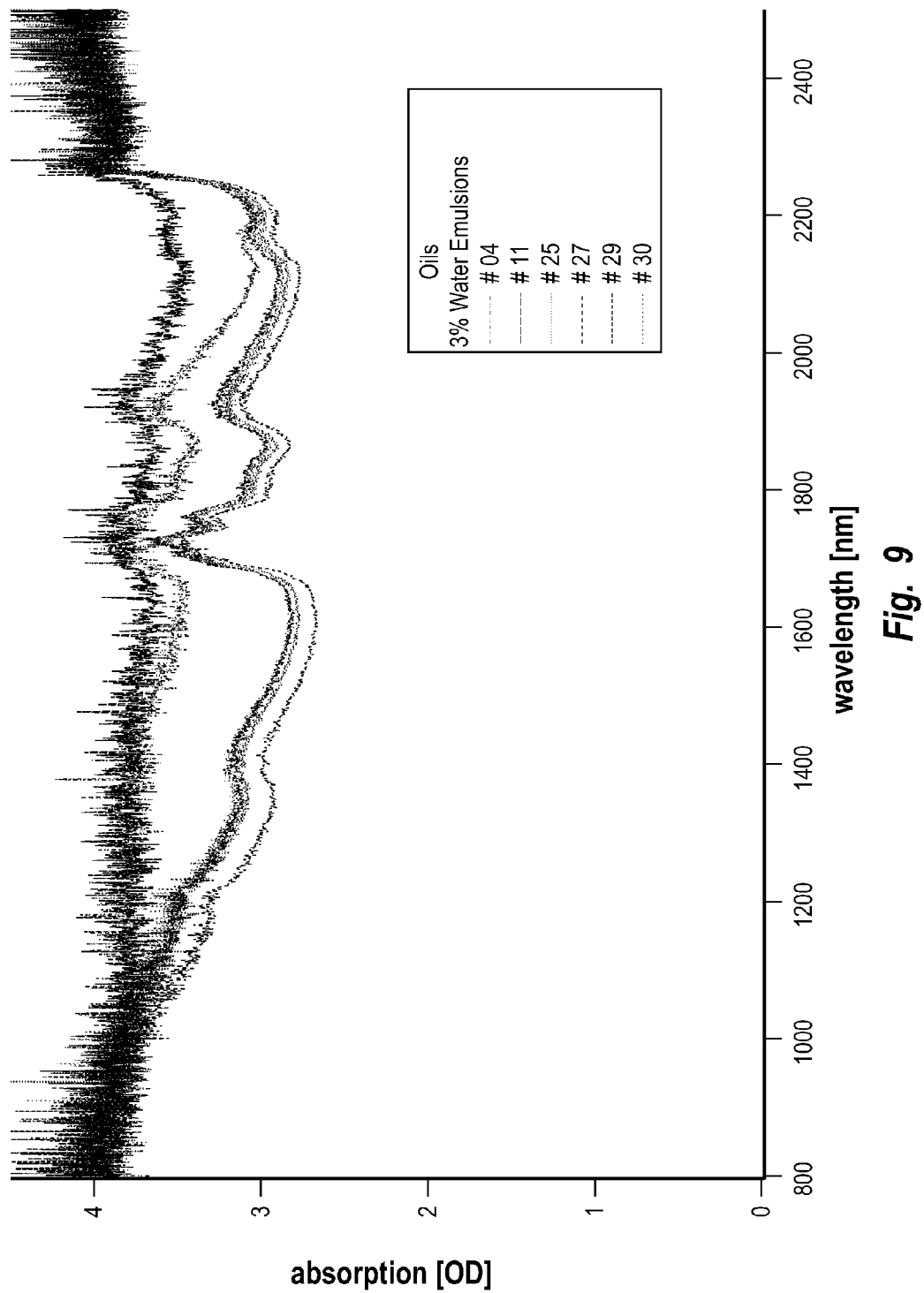
FIG. 9 shows absorption spectra for the same six Middle Eastern oils identified in FIG. 5 after addition of a 3% water emulsion.

FIG. 9 is an absorption spectra for the same six Middle Eastern oils identified above after addition of a 3% water emulsion. The water droplets (approx. 1 micron size) produce intense scattering, which severely distorts the absorption spectrum and renders the sample opaque with a resulting loss of information content. The scattering background and water peaks cannot be reliably backed out, to reveal the true color of the oil.

Figure 10:
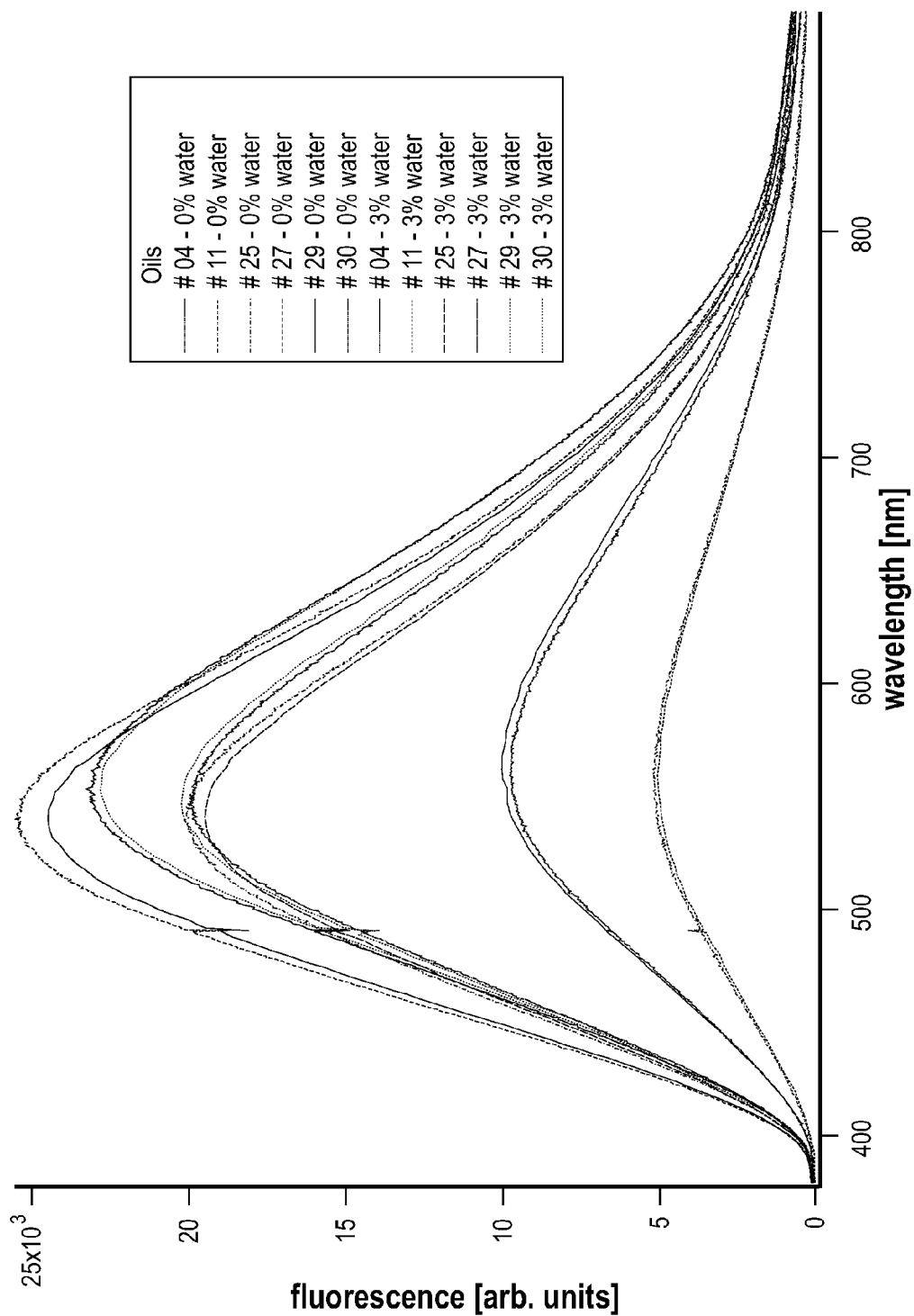
FIG. 10 compares the fluorescence intensity with (solid lines) and without (dashed lines) a 3% water/oil emulsion for the same six oils in FIG. 9.

FIG. 10 compares the fluorescence intensity with (solid lines) and without (dashed lines) of a 3% w/o emulsion. The fluorescence signal shows some slight increase but which contributes an offset and does not affect the relative fluorescence intensities and leaves the line-shape unchanged. Water does not fluoresce at visible wavelengths, and the fluorescent photons which escape self-absorption also experience less scattering in a front surface geometry. Thus fluorescence can be used to map compositional variations accurately even when emulsions are present. It is therefore possible for those of ordinary skill in the art having the benefit of this disclosure to detect color (and composition), gradients, or other characteristics in an oil column in the presence of emulsions by using fluorescence logs.

Figure 11:
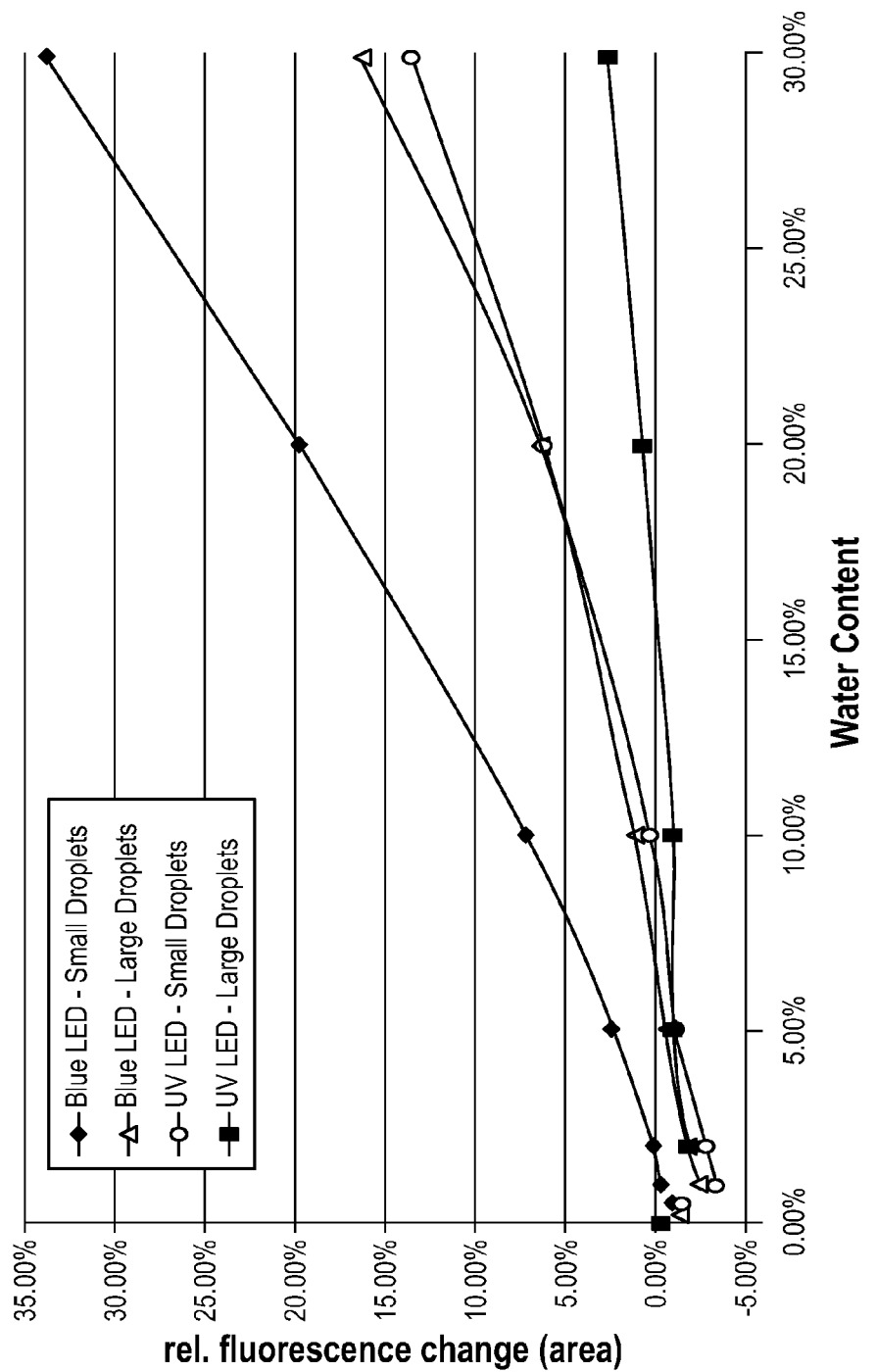
FIG. 11 compares the fluorescence sensitivity as a function of water fraction for different wavelengths, and droplet size distributions.

FIG. 11 compares the fluorescence sensitivity as a function of water fraction for different wavelengths and droplet size distributions. Large droplets produce less scattering than small ones. Shorter wavelength UV excitation results in less scattering than the blue wavelength radiation.

As mentioned above, Schlumberger's CFA™ has a fluorescence sensor, which may perform fluorescence spectroscopy by measuring light emission in the green and red ranges of the spectrum after excitation with blue light. Fluorescence in this range is related to the concentration of polycyclic aromatic hydrocarbons (PAH's) in the crude oil. Fluorescence was initially introduced to detect phase transitions particularly in gas condensate systems while sampling. When a phase transition occurs in a retrograde condensate fluid, the newly formed liquid phase will concentrate the heaviest components of the original fluid. As was previously mentioned, these heavy components contain the molecular groups that fluoresce. Fluorescence measurements are highly sensitive—even more so than other types of spectroscopy such as absorption spectroscopy—therefore making it possible to detect the slightest changes in the composition of the fluid being assayed.

Based on the above measurement principles and extensive observations from field practices, several features of CFA™ fluorescence emerge:

Fluorescence does not suffer from strong scattering usually caused by mud solids. Mud solids very likely do not have any PAH's Fluorescence measurements in a borehole are less affected by water droplets in water-oil emulsions than corresponding absorption measurements. This feature allows one to identify oil properties even when oil and water emulsions exist.

Fluorescence can be used to type different hydrocarbons such as gas (it should be noted that gas is a fluid), condensate, light oil and black oil. In simple words, gases usually have little or no heavy components, hence very little PAH's. Therefore, gas should have very weak fluorescence. Oil typically has more heavy components, hence much more PAH's. Accordingly, oils should have much stronger fluorescence than gases.

Fluorescence is highly sensitive. Therefore, it can detect very small oil droplets mixed with water.

Moreover, fluorescence will not react on OBM (oil based mud) because OBM typically should not contain any PAH's.

The preceding description has been presented only to illustrate and describe certain embodiments. It is not intended to be exhaustive or to limit the invention to any precise form disclosed. Many modifications and variations are possible in light of the above teaching.

The embodiments and aspects were chosen and described in order to best explain the principles of the invention and its practical application. The preceding description is intended to enable others skilled in the art to best utilize the principles in various embodiments and aspects and with various modifications as are suited to the particular use contemplated.

What is claimed is:

1. A method of analyzing fluid properties, the method comprising:
   providing a downhole fluid analysis tool;
   extracting a fluid from a downhole formation with the downhole fluid analysis tool;
   flowing the fluid into the downhole fluid analysis tool;
   acquiring a fluorescence signal from the fluid while downhole to analyze at least one fluid property;
   moving the downhole fluid analysis tool through a borehole; and
performing the extracting, flowing, and acquiring at multiple locations along the borehole.

2. The method according to claim 1, wherein acquiring the fluorescence signal comprises irradiating the fluid through an optical cell and detecting the fluorescence signal.

3. The method according to claim 1, further comprising:
   comparing the fluorescence signal to a known fluorescence spectra;
identifying the fluid based on the comparison of the fluorescence signal of the fluid to the known fluorescence spectra.

4. The method according to claim 1, further comprising:
   comparing the fluorescence signal to a known fluorescence spectra while down hole;
   identifying the fluid based on the comparison of the fluorescence signal of the fluid to the known fluorescence spectra while downhole.

5. The method according to claim 1, further comprising:
correlating the fluorescence signal and other physical characteristics of the fluid to generate at least one datapoint.

6. The method according to claim 5, wherein the other physical characteristics comprise one of density, viscosity, C36+ or some combination thereof.

7. The method according to claim 1, further comprising correlating the fluorescence signal with one of other well-logging data or logging-while-drilling data.

8. The method according to claim 7, further comprising correlating the fluorescence signal with the other well-logging data or logging-while-drilling data and identifying relationships between the fluorescence signal and the well-logging data or logging-while-drilling data.

9. The method according to claim 7, further comprising correlating the fluorescence signal with the other well-logging data or the logging-while-drilling data and creating at least one model, table or both to assist in interpreting the fluorescence signal.

10. A method of identifying fluid compositional gradients in an oil column, the method comprising:
moving a fluid analysis tool through a borehole;
setting the fluid analysis tool at a desired sampling interval of the borehole;
extracting a fluid from a formation adjacent to the borehole into a flowline in a body of the fluid analysis tool;
irradiating the fluid in the flowline through an optical cell inserted in the flowline;
detecting fluorescence, wherein said detected fluorescence is used in identifying one or more fluid compositional gradient.

11. The method according to claim 10, further comprising identifying the one or more fluid compositional gradient in a fluid column by comparing the fluorescence signals along the sampling interval of the borehole.

12. The method according to claim 10, further comprising:
comparing the detected fluorescence to a known fluorescence spectra;
identifying the fluid based on the comparison of the detected fluorescence to the known fluorescence spectra.

13. The method according to claim 10, wherein a distance between the settings on the sampling interval is regular or irregular.

14. The method according to claim 10, wherein the irradiation is accomplished with a UV wavelength light.

15. A method of analyzing a formation sample, the method comprising:
acquiring fluorescence data from the formation sample while downhole at multiple stations;
analyzing changes in fluorescence at two or more of the multiple stations; and
comparing said analyzed changes in fluorescence at two or more of the multiple stations.

16. The method according to claim 15, further comprising:
measuring color of the formation sample at the multiple stations;
relating changes in the fluorescence data to changes in fluid color.

17. The method according to claim 15, further comprising using changes in the fluorescence data to determine if there are fluid compartments within a formation.

18. The method according to claim 15, further comprising:
analyzing a structure of the fluorescence data over an extended depth interval;
producing an indication of a physical property correlated with fluorescence.

19. The method according to claim 15, further comprising:
correlating the fluorescence data with other well-logging data so as to obtain correlated fluorescence data;
identifying relationships between the fluorescence data and the other well-logging data so as to obtain identified relationship fluorescence data;
creating one or more models based on the correlated fluorescence data, identified relationship fluorescence data or both.

20. The method according to claim 15, wherein the fluorescence data is used to form a quasi-continuous log.

21. The method according to claim 15, wherein the formation sample contains a water/oil emulsion.

22. A downhole fluid analysis tool, comprising:
a fluid extraction module having a flowline, wherein a fluid is extracted from a first location of a formation of one or more locations in the formation, such that the fluid flows into the downhole fluid analysis tool;
an optical cell disposed in the flowline;
an irradiation source at the optical cell; and
a fluorescence detection unit at the optical cell which acquires a fluorescence signal from the fluid while downhole to analyze at least one fluid property;
wherein the downhole fluid analysis tool is positioned through a borehole at another location of the formation of the one or more locations in the formation, so that the fluorescence detection unit acquires another fluorescence signal while downhole to analyze the at least one fluid property.

23. The downhole fluid analysis tool according to claim 22, further comprising a fluid color measurement module.

24. The downhole fluid analysis tool according to claim 22, wherein the irradiation source comprises an LED or laser diode capable of producing one of a visible light, a ultraviolet light, or a infrared light.

25. A method for retrofitting a tool for analyzing fluid properties, the method comprising:
retrofitting the tool with a fluorescence detection unit, wherein the tool is an existing downhole fluid analysis tool;
extracting a fluid from a formation with the retrofitted tool;
flowing the fluid into the retrofitted tool;
acquiring a fluorescence signal from the fluid while downhole to analyze at least one fluid property;
moving the retrofitted tool through a borehole; and
performing the extracting, flowing, and acquiring at multiple locations along the borehole.

26. The method according to claim 25, further comprising retrofitting the tool with a UV light source.

27. A method of analyzing fluid properties, the method comprising:
providing a fluid analysis tool;
extracting a fluid from a downhole location with the fluid analysis tool;
flowing the fluid into the fluid analysis tool;
acquiring a fluorescence signal from the fluid while downhole to analyze at least one fluid property;
moving the fluid analysis tool through a borehole;
performing the extracting, flowing, and acquiring at multiple locations along the borehole; and
identifying fluid compositional gradients in a fluid column by comparing the fluorescence signals at two or more of the multiple locations along the borehole.

28. A method of analyzing fluid properties, the method comprising:
  providing a fluid analysis tool;
  extracting a fluid from a subterranean location with the fluid analysis tool;
  flowing the fluid into the fluid analysis tool;
  acquiring a fluorescence signal from the fluid while downhole to analyze at least one fluid property;
  moving the fluid analysis tool through a borehole;
  performing the extracting, flowing, and acquiring at multiple locations along the borehole;
  flowing the fluid back out of the fluid analysis tool; and
  generating a quasi-continuous log of the fluid without collecting samples.

* * * * *